(12) United States Patent
Ljuhar

(10) Patent No.: US 9,308,544 B2
(45) Date of Patent: Apr. 12, 2016

(54) ATOMIZATION DEVICE

(71) Applicant: Braincon Handels-GmbH, Vienna (AT)

(72) Inventor: Davul Ljuhar, Vienna (AT)

(73) Assignee: Braincon Handels-GmbH, Vienna (AT)

( * ) Notice: Subject to any disclaimer, the term of this patent is extended or adjusted under 35 U.S.C. 154(b) by 0 days.

(21) Appl. No.: 14/361,752

(22) PCT Filed: Nov. 30, 2012

(86) PCT No.: PCT/AT2012/050188
§ 371 (c)(1),
(2) Date: May 30, 2014

(87) PCT Pub. No.: WO2013/078495
PCT Pub. Date: Jun. 6, 2013

(65) Prior Publication Data
US 2014/0326802 A1    Nov. 6, 2014

(30) Foreign Application Priority Data
Dec. 2, 2011    (AT) ................................ A 1789/2011

(51) Int. Cl.
| | | |
|---|---|---|
| *B05B 1/08* | (2006.01) | |
| *B05B 17/06* | (2006.01) | |
| *B05B 7/00* | (2006.01) | |
| *A61L 9/14* | (2006.01) | |

(52) U.S. Cl.
CPC ............... *B05B 17/0615* (2013.01); *A61L 9/14* (2013.01); *B05B 7/0012* (2013.01); *A61L 2209/135* (2013.01)

(58) Field of Classification Search
USPC ...................................................... 239/102.2
See application file for complete search history.

(56) References Cited

U.S. PATENT DOCUMENTS

| | | | | |
|---|---|---|---|---|
| 5,823,179 | A | * | 10/1998 | Grychowski et al. ..... 128/200.18 |
| 6,123,269 | A | * | 9/2000 | Schmitkons et al. ............. 239/3 |
| 6,338,443 | B1 | * | 1/2002 | Piper ............................. 239/340 |
| 7,267,120 | B2 | * | 9/2007 | Rustad et al. ............ 128/200.18 |
| 2002/0157663 | A1 | * | 10/2002 | Blacker et al. ........... 128/200.21 |
| 2003/0136399 | A1 | * | 7/2003 | Foley et al. .............. 128/200.14 |
| 2005/0166918 | A1 | * | 8/2005 | Trombi .................... 128/203.12 |
| 2009/0053397 | A1 | | 2/2009 | Buchner et al. |

FOREIGN PATENT DOCUMENTS

| | | |
|---|---|---|
| DE | 102005019686 B3 | 4/2006 |
| GB | 525736 A | 9/1940 |

(Continued)

OTHER PUBLICATIONS

Austrian Search Report issued on Nov. 15, 2012 in Austrain Application No. A 1789/2011.

(Continued)

*Primary Examiner* — Len Tran
*Assistant Examiner* — Adam J Rogers
(74) *Attorney, Agent, or Firm* — Panitch Schwarze Belisario & Nadel LLP

(57) ABSTRACT

An atomizer is provided having an atomization chamber (1, 2; 1') for receiving a liquid, at least one nebulizer (3, 4; 4') for atomizing the liquid into drops of liquid, and an exit port (30) for discharging the vapor or mist of liquid thus generated from the atomization chamber (1, 2; 1'). At least one device for deflecting the vapor or mist of liquid (5; 5') is provided, which is arranged in the area above the liquid surface.

8 Claims, 3 Drawing Sheets

(56) References Cited

FOREIGN PATENT DOCUMENTS

| WO | 92/10301 A1 | 6/1992 |
| WO | 93/06721 A1 | 4/1993 |
| WO | 2009013843 A1 | 1/2009 |

OTHER PUBLICATIONS

Int'l Preliminary Report on Patentability issued Jun. 2, 2014 in Int'l Application No. PCT/AT2012/050188.
Int'l Search Report issued Apr. 10, 2013 in Int'l Application No. PCT/AT2012/050188.

* cited by examiner

ATOMIZATION DEVICE

CROSS-REFERENCE TO RELATED APPLICATIONS

This application is a Section 371 of International Application No. PCT/AT2012/050188, filed Nov. 30, 2012, which was published in the German language on Jun. 6, 2013, under International Publication No. WO 2013/078495 A1 and the disclosure of which is incorporated herein by reference.

BACKGROUND OF THE INVENTION

The invention relates to an atomizer having an atomization chamber for receiving a liquid and at least one nebulizer for atomizing the liquid into drops of liquid, as well as an exit port for discharging the vapor or mist of liquid thus generated from the atomization chamber.

For the purpose of killing dangerous particles such as viruses, spores, bacteria, etc. in rooms or for the disinfection of rooms and surfaces, the vapor or mist of liquid discharged by such a known atomizer is allowed to react in a room or surroundings. For example, a liquid suitable for disinfection is distributed evenly in the ambient air in the form of droplets, as an aerosol, so that it encounters, for example, infectious particles, in the air or on surfaces, which infectious particles are rendered innocuous by the disinfecting effect of the liquid.

Droplet size and their size distribution have been disadvantageous up to now because they are controllable only very poorly by conventional atomizers. The atomization process by ultrasonic transformers produces not only small droplets, but also bigger ones that deposit relatively strongly on surfaces, which is undesirable because it creates humidity which can be disadvantageous in various aspects. Sensitive surfaces may be destroyed, or a corrosion process may be initiated on valuable objects or instruments.

The smaller the droplet size can be kept, the less humidity or liquid deposition develops in the surroundings where the atomizer is to take effect.

BRIEF SUMMARY OF THE INVENTION

It is thus the object of the invention to provide an atomizer of the above type, by which a mist of liquid having a droplet diameter as small as possible can be discharged into the surroundings.

According to the invention this is achieved by arranging at least one device for deflecting the vapor or mist of liquid in the area above the liquid surface.

A deposition of droplets having larger diameters is formed on this deflecting device, so that a mist of liquid having substantially smaller droplets remains.

The average diameter of the droplets of liquid can thus be reduced to less than 1 µm, so that a mist of liquid is created that is felt to be very dry, and thus in the following referred to as dry vapor, which does not form any film of moisture on the surface to be treated that could lead to the development of mold or rust.

In contrast to common devices based on vapor, however, the liquid does not have to be heated for generating the dry vapor.

In a further embodiment of the invention the at least one device for deflecting the vapor or mist of liquid can be formed by a turbulence shield arranged above the liquid level in the interior of the atomization chamber, at which larger liquid droplets can form a precipitate and run or drip off.

In order to remove larger droplets very efficiently, the turbulence shield can, according to a further embodiment of the invention, have a horizontal wall section and a wall section connected thereto and inclined towards the liquid surface, wherein the inclined wall section is especially well suited for deflecting the created dry vapor towards the exit port and at the same time allowing the larger droplets to be separated, wherein deposited droplets run or drip back into, for example, a tub in which the liquid is received.

In particular, when according to a further embodiment of the invention, the inclined wall section extends above the at least one nebulizer, which is arranged in the bottom area of the atomization chamber, this allows an extremely strong reduction of the proportion of large droplet diameters in the created dry vapor.

In this connection it has proven especially preferable to have the inclined wall section inclined at an angle of $\beta 1$ with regard to the horizontal, with $\beta 1$ being in the range of 10° to 45°.

In order to draw off the mist of liquid freed from the larger droplets, a through-flow is introduced which sets the created aerosol into motion.

For this purpose, according to another exemplary embodiment of the invention, an opening is formed in the atomization chamber, through which an airflow can be passed over the liquid surface.

Advantageously, it can be provided that the free end of the turbulence shield projecting into the atomization chamber is arranged at a distance from a side wall of the atomization chamber forming an opening cross-section, so that the atomization chamber is separated into an upper and a lower area except for the opening cross-section.

Furthermore, a pressure device may be arranged in the upper area of the atomization chamber, via which the pressure within the atomization chamber is increased to create an airflow.

In a further embodiment of the invention, the pressure device can be formed by at least one fan, via which air is blown into the atomization chamber from the surroundings, so that an airflow is created through the opening cross-section, which moves the vapor or mist of liquid ascending from the liquid towards the exit port.

According to another embodiment, the exit port can be formed at one end of a discharge box having a rectangular pipe cross-section extending upwards. The mist of liquid freed from larger droplet diameters is discharged to the surroundings via this discharge box. Also, instead of the rectangular pipe cross-section a different, for example circular, cross-section can be contemplated.

A further fluid-engineering measure for reducing the proportion of droplets of liquid having large diameters can be provided by forming an acceleration prism in the area of the exit port that projects above the liquid level.

It is especially preferred that the acceleration prism be formed by two legs in the form of an inverted V cross section, wherein the legs are inclined with regard to the vertical at an angle of $\delta 1$.

In order to allow further removal of droplets having larger diameters from the mist of liquid, it can be provided that the acceleration prism with its leg facing the exit port forms a cross-sectional narrowing having a width of a1 of the atomization chamber.

Finally, an increase of the exit velocity of the mist of liquid is guaranteed by the fact that, according to a further development of the invention, a rectangular flow hollow profile is arranged on at least one side of the discharge box, the lower end of which is connected to the upper part of the atomization chamber, so that a partial flow of the pressure device is led through the flow hollow profile.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

FIGS. 1 to 4 show an embodiment of an inventive atomizer by which a liquid can be atomized and delivered to the surroundings in the form of droplets of liquid, for example to decontaminate or disinfect a room, in that the droplets of liquid destroy particles floating in the air or adhering to surfaces so that they become ineffective for humans or animals, which prevents them from attacking cells and exerting their detrimental effects there. Food or computer keyboards, for example, can also be freed from dangerous germs or other particles by exposing them to mist or vapor of liquid discharged by the inventive atomizer.

Irrespective of the type of particles, such as viruses, fungi, bacteria, etc., the atomizer expels a continuous flow of droplets of liquid, which spread correspondingly and exert their disinfecting effect. The liquid to be atomized can, for example, be hydrogen peroxide, but other liquids or mixtures of liquids or pure water, which has no disinfecting effect, can also be atomized.

Figure 1:
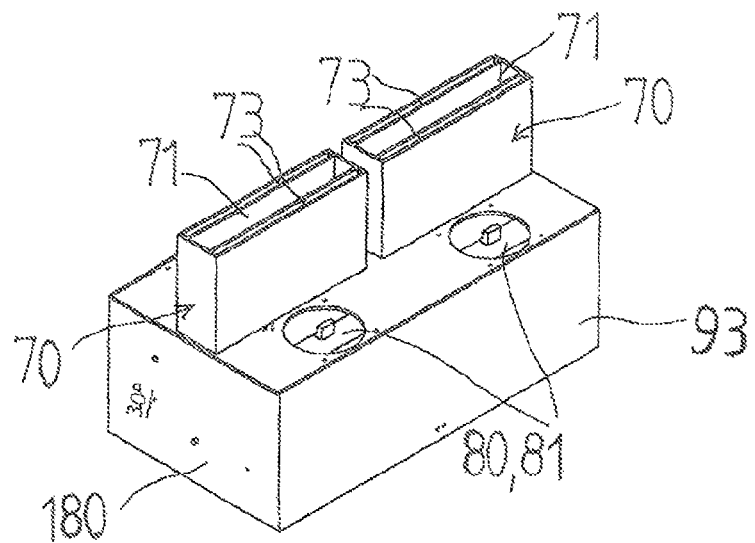
FIG. 1 is a top perspective view showing an atomizer according to one embodiment of the invention.
Figure 2:
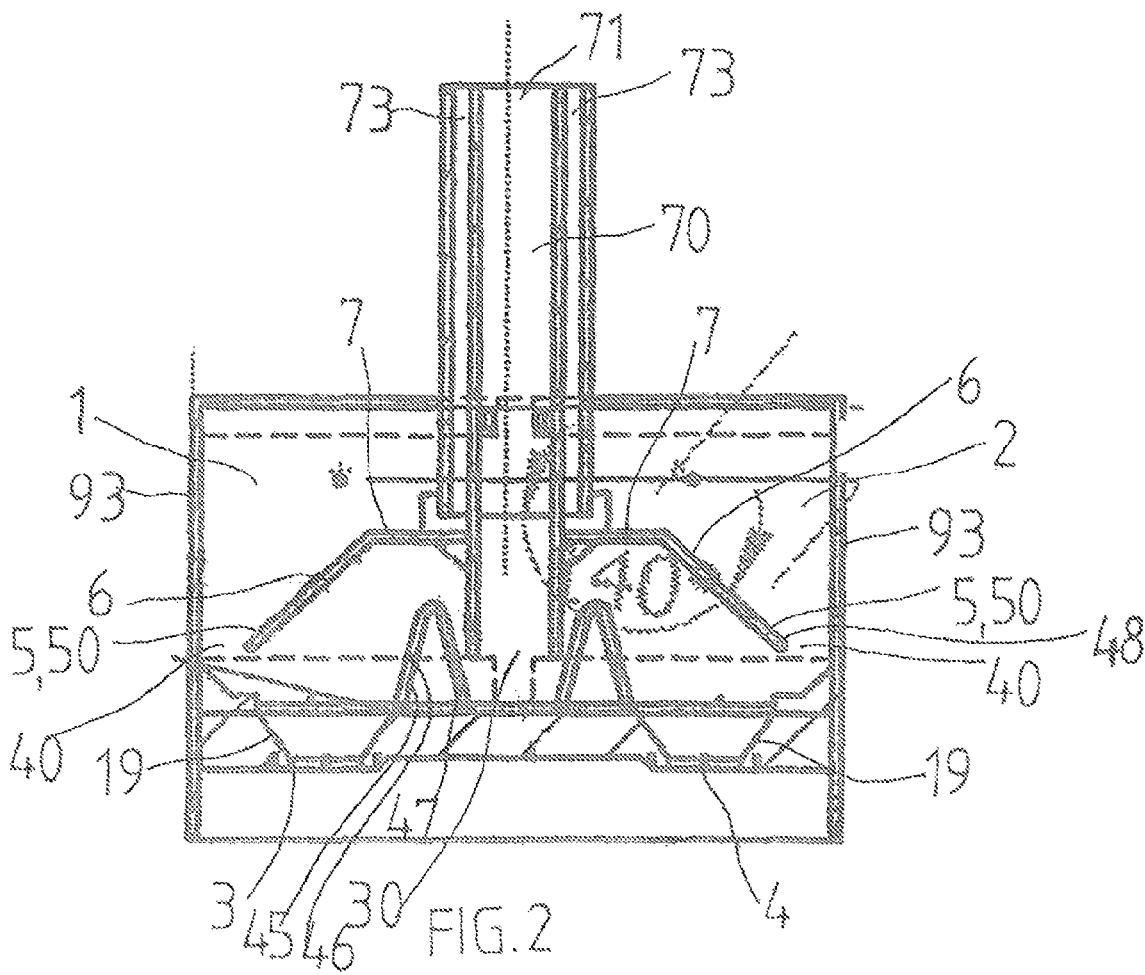
FIG. 2 is a sectional view perpendicular to the longitudinal axis through the atomizer according to FIG. 1.

The atomizer shown in FIGS. 1 to 4 is enclosed by a housing 180 and has two atomization chambers 1, 2 in its interior for receiving the liquid, which atomization chambers 1, 2 are arranged mirror-symmetrically with regard to the central plane, as may be seen in FIG. 2. It is also possible to provide only one or more than two atomization chambers without affecting the mode of action of the atomizer.

During operation, the two atomization chambers 1, 2 are filled with a liquid up to a predetermined liquid level. For this purpose, the bottom area of the atomization chambers 1, 2 has a tub-like shape. When the level has fallen to a certain extent, a refill is required.

In parallel with the longitudinal axis of the atomizer, respective pluralities of adjacently arranged nebulizers 3, 4 are provided in the atomization chambers 1, 2 (FIG. 4), in the shown example e.g. as ultrasonic nebulizers. Within the framework of the invention, however, a different type of atomization, e.g. an electrostatic form, can also be used.

The nebulizers 3, 4, which can, for example, be provided as piezoelectric elements, are recessed into the bottom of the atomization chambers 1, 2, so that they contact the liquid with their vibration bodies and set it into vibration. Thus, an atomization process takes place during which small droplets dissociate from the liquid surface and are cast upwards, which forms an aerosol.

For improving the mode of action of the nebulizers 3, 4, a sound-reflecting cone 19 is formed between them and the chamber bottom, by which the sound waves produced by the nebulizers 3, 4 are bundled. The cone 19 can, however, also be emitted.

A cone angle $\phi 1$ (FIG. 3) in the range of 15° to 80° has proven particularly advantageous, but other angle values may also be used.

The developing dry vapor moves through an exit port 30, which is formed at the lower end of a discharge box 70, which is divided into two partial boxes in the exemplary embodiment shown in FIGS. 1 to 4, having a rectangular pipe cross-section extending upwards.

According to the invention, a device for deflecting the vapor or mist of liquid 5 is provided, which is arranged in the area above the liquid surface.

In the exemplary embodiment that is shown the device for deflecting the vapor or mist of liquid 5 is formed by a turbulence shield 50 arranged above the liquid level in the interior of the atomization chambers 1, 2, which shield has a horizontal wall section 6 and a wall section 7 connected thereto and inclined towards the liquid surface. However, a different type of deflection may also be provided.

Figure 3:
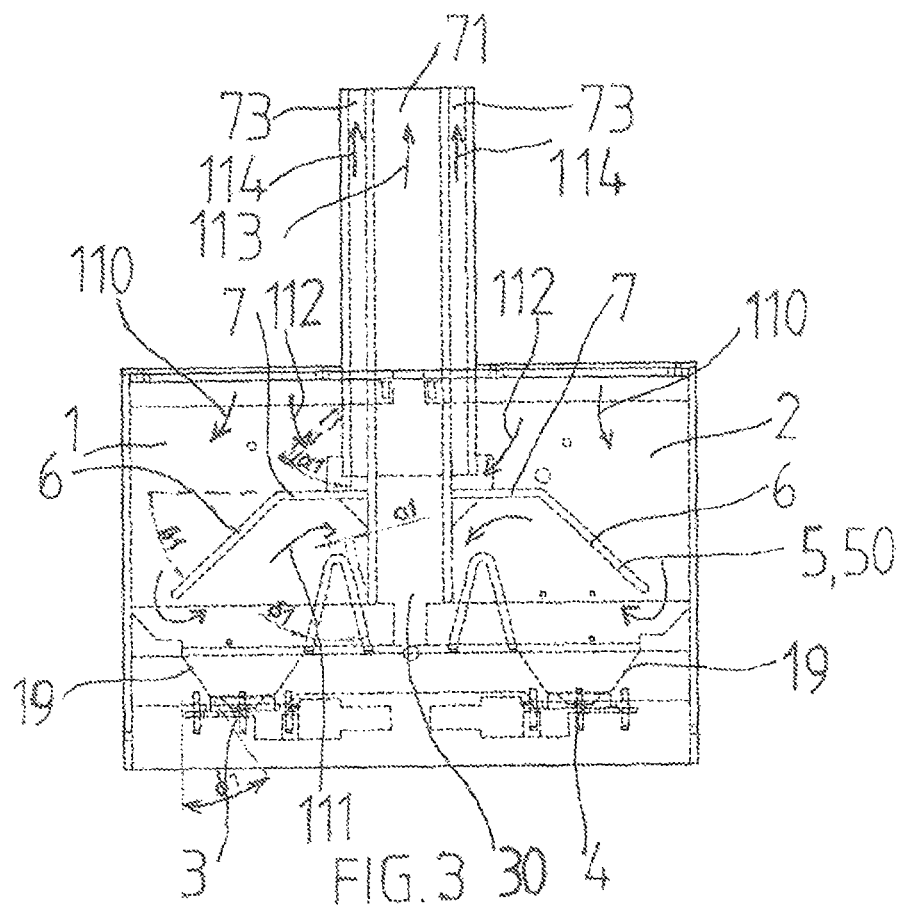
FIG. 3 is a sectional view taken along line BB of FIG. 4.
Figure 4:
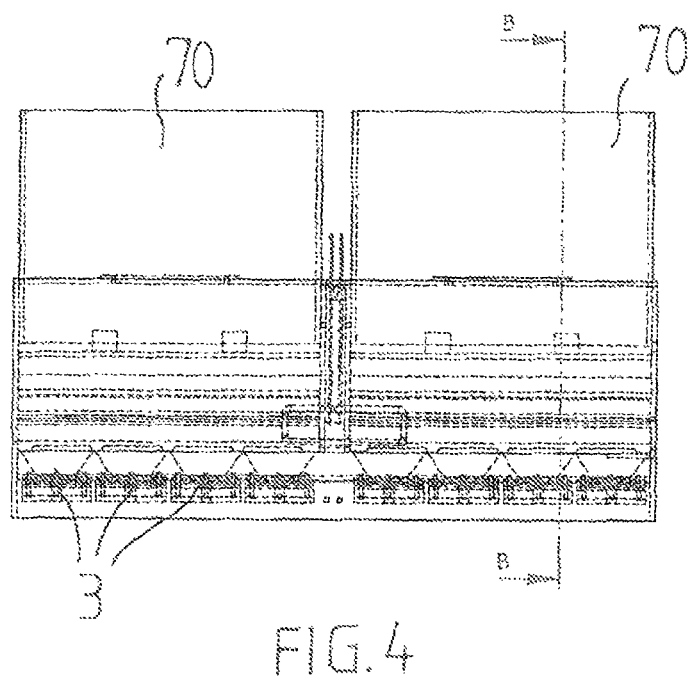
FIG. 4 is a lateral view of the embodiment of FIG. 1.
Figure 5:
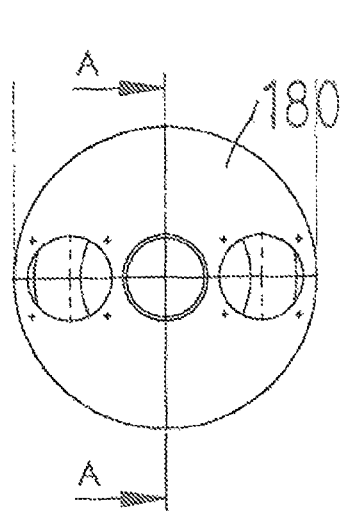
FIG. 5 is a top view of an atomizer according to another embodiment of the invention.
Figure 6:
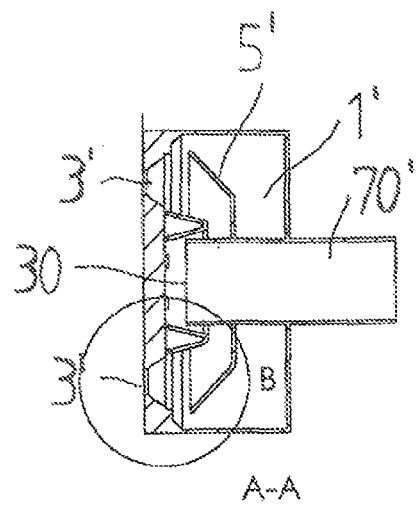
FIG. 6 is a sectional view taken along line AA of FIG. 5.
Figure 7:
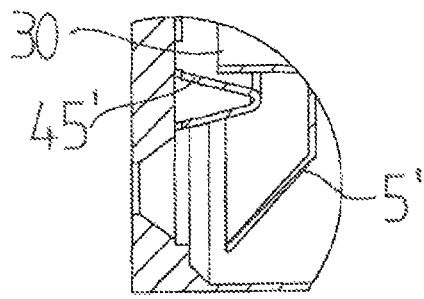
FIG. 7 is an enlarged view of the detail B of FIG. 6.
Figure 8:
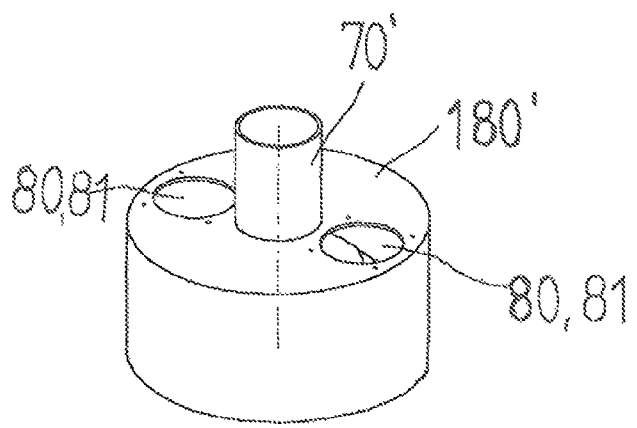
FIG. 8 is a top perspective view of the embodiment of FIG. 5.

The inclined wall section 7 extends above the nebulizers 3, 4, which are arranged in the bottom area of the atomization chamber 1, 2, and is inclined at an angle of $\beta 1$ with regard to the horizontal, with $\beta 1$ being in the range of 10° to 45°. In FIGS. 2 and 3, the angle $\beta 1$ is chosen to be 40°.

Dry vapor ascending from the liquid surface is deflected by the inclined wall section 7 towards the exit port 30. Larger droplets adhere to the underside of the inclined wall section 7 and run off along the inclined wall section 7 downwards towards the liquid. The rest of the mist thus contains fewer droplets having large diameters, so that it can be referred to as dry vapor.

The free ends of the turbulence shield 50 projecting into the atomization chambers 1, 2 are each arranged at a distance from a side wall 93 of the atomization chambers 1, 2 forming opening cross-sections, so that the atomization chambers 1, 2 are separated into an upper and a lower area except for the opening cross-section. Respective pressure devices 80 may be arranged in the upper areas of the atomization chambers, via which the pressure within the atomization chambers 1, 2 is increased during operation.

The pressure device 80 is formed by one or more fans 81 via which air is blown into the atomization chamber from the surroundings, so that an airflow is created through the opening cross-section 40, which moves the vapor or mist of liquid ascending from the liquid towards the exit port 30.

An acceleration prism 45 is formed in the area of the exit port 30 that projects above the liquid level and is formed by two legs 46, 47 in the form of an inverted V cross section, wherein the legs 46, 47 are inclined with regard to the central axis or the vertical at an angle of $\delta 1$. The angle of $\delta 1$ may be in a preferred range of 0° to 60°.

At this acceleration prism 45, atomized droplets of fluid having a larger diameter also form a deposition, while the finer droplets reach the exit port 30 via this acceleration prism 45. Simultaneously, the acceleration prism 45 with its leg 47 facing the exit port 30 and the lower end of the discharge box 70 forms a tapering cross-sectional narrowing having a width of $a1$ at the lower edge of the discharge box 70. The exit port 30 is at approximately halfway up the acceleration prism 45. The cross-sectional narrowing width a1 can preferably be selected in a range of 1 mm to 15 mm, but other dimensions are also possible. The design of the acceleration prism 45 can also be different within the framework of the invention and can, for example, be formed without being supported on the tub bottom.

Altogether, the atomized droplets of liquid are moved under the effect of the airflow (arrow 110) created by the pressure device as an aerosol flow (arrow 111) towards the exit port 30, through which they arrive in the discharge box 70, through which they arrive at the upper end of the discharge box 70 (arrow 113), where a discharge opening 71 is formed, through which the dry vapor is discharged to the surroundings.

The lower end of the discharge box 70 can also be expanded, as is shown by the angle of $\alpha 1$, which in the exemplary embodiment shown is 0°. $\alpha 1$ in the range of 0° to 45° has proven to be preferable.

An additional measure for accelerating the exit of the mist of fluid from the discharge opening 71 is the arrangement of rectangular flow hollow profiles 73 on the longitudinal sides of the discharge box 70, the lower ends of which are each connected to the upper parts of the atomization chambers 1, 2, so that a partial flow (arrow 112) of the pressure device 80 is introduced into the flow hollow profile and led therethrough (arrow 114), so that a suction effect at the discharge opening 71 of the discharge box 70 occurs, which increases the exit velocity of the dry vapor.

FIGS. 5 to 8 show a further exemplary embodiment of the inventive atomizer having a cylindrical housing 180', which receives a circular atomization chamber 1'. A deflection device 5' having the shape of a hollow truncated cone is arranged in the area above the liquid surface. In addition, a circular acceleration prism 45' is arranged in the area of the exit port 30, which is formed by the lower end of a hollow-cylindrical discharge pipe 70'. The nebulizers 3' are in a circular arrangement. The mode of action corresponds to the embodiments shown in FIGS. 1 to 4. Similarly, the angle ranges for $\alpha 1$, $\beta 1$, $\delta 1$, $\phi 1$ and the width ranges a1 given as preferred ranges are also preferred for the exemplary embodiment according to FIGS. 5 to 8, so that the angles shown in FIGS. 5 to 8 are merely to be regarded as possible variations.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An atomizer comprising:

an atomization chamber for receiving a liquid;

at least one nebulizer for atomizing the liquid into a vapor; and an exit port for discharging the vapor thus generated from the atomization chamber, wherein at least one device for deflecting the vapor is arranged in an area above a surface of the liquid, wherein an acceleration prism formed in an area of the exit port projects above the liquid level and is arranged such that a cross-sectional narrowing of the atomization chamber is formed, wherein the at least one device for deflecting the vapor comprises a turbulence shield arranged above the liquid surface in an interior of the atomization chamber, a free end of the turbulence shield projecting into the atomization chamber is arranged at a distance from a side wall of the atomization chamber to form an opening cross-section, such that the atomization chamber is separated into an upper region and a lower region except for the opening cross-section, wherein the turbulence shield has a horizontal wall section and an inclined wall section connected thereto and inclined towards the liquid surface, and wherein the vapor ascending from the liquid is moved towards the exit port via a pressure device arranged in the upper region of the atomization chamber, via which pressure within the atomization chamber is increased, the pressure device comprising at least one fan, via which air is blown into the atomization chamber from its surroundings, such that an airflow is created through the opening cross-section, which moves the vapor ascending from the liquid towards the exit port.

2. The atomizer according to claim 1, wherein the acceleration prism comprises two legs in a form of an inverted V cross section, and wherein the cross-sectional narrowing is formed in an area of one of the legs of the acceleration prism facing the exit port.

3. The atomizer according to claim 2, wherein the legs are inclined at an angle $\delta 1$ of 0° to 60° with respect to vertical.

4. The atomizer according to claim 1, wherein the cross-sectional narrowing of the atomization chamber has a width a1 of 1 mm to 15 mm.

5. The atomizer according to claim 1, wherein the inclined wall section extends above the at least one nebulizer, which is arranged in a bottom area of the atomization chamber.

6. The atomizer according to claim 5, wherein the inclined wall section is inclined at an angle $\beta 1$ in a range of 10° to 45° with respect to horizontal.

7. The atomizer according to claim 1, wherein the exit port is formed at one end of a discharge box having a rectangular pipe cross-section extending upwards.

8. The atomizer according to claim 7, wherein a rectangular flow hollow profile is arranged on at least one side of the discharge box, a lower end of the flow hollow profile being connected to the upper region of the atomization chamber, such that a partial flow of the pressure device is led through the flow hollow profile.

* * * * *